US006960020B2

(12) United States Patent
Lai

(10) Patent No.: US 6,960,020 B2
(45) Date of Patent: Nov. 1, 2005

(54) IMAGE POSITIONING METHOD AND SYSTEM FOR TOMOSYNTHESIS IN A DIGITAL X-RAY RADIOGRAPHY SYSTEM

(75) Inventor: Ching-Ming Lai, Wakefield, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/232,266

(22) Filed: Aug. 30, 2002

(65) Prior Publication Data

US 2003/0043962 A1     Mar. 6, 2003

Related U.S. Application Data

(60) Provisional application No. 60/316,511, filed on Aug. 31, 2001.

(51) Int. Cl.[7] .......................... G01D 18/00; H05G 1/64
(52) U.S. Cl. .......................... 378/207; 378/21; 378/22; 378/25; 378/26; 378/163
(58) Field of Search .................... 378/21–27, 162–164, 378/205, 207, 37, 197; 250/252.1; 600/425, 600/426

(56) References Cited

U.S. PATENT DOCUMENTS

| 4,419,577 | A | * | 12/1983 | Guth ........................ 250/252.1 |
| 5,008,947 | A | * | 4/1991 | Yamada ........................ 382/132 |
| 5,052,035 | A | * | 9/1991 | Krupnick ..................... 378/163 |
| 5,239,569 | A | | 8/1993 | Saleh et al. .................. 378/163 |
| 5,359,637 | A | * | 10/1994 | Webber .......................... 378/2 |
| 5,561,698 | A | * | 10/1996 | Mick et al. .................. 378/162 |
| 5,760,403 | A | * | 6/1998 | Elabd ..................... 250/370.11 |
| 5,841,835 | A | * | 11/1998 | Aufrichtig et al. .......... 378/207 |
| 5,872,828 | A | * | 2/1999 | Niklason et al. .............. 378/23 |
| 5,964,715 | A | * | 10/1999 | Thunberg .................... 600/562 |
| 6,081,577 | A | * | 6/2000 | Webber ....................... 378/23 |
| 6,196,715 | B1 | | 3/2001 | Nambu et al. ............... 378/197 |
| 6,459,760 | B1 | * | 10/2002 | D'Ambrosio ................ 378/43 |
| 6,652,142 | B2 | * | 11/2003 | Launay et al. .............. 378/205 |
| 6,671,349 | B1 | * | 12/2003 | Griffith ........................ 378/163 |
| 6,862,337 | B2 | * | 3/2005 | Claus et al. ................... 378/26 |

* cited by examiner

Primary Examiner—Allen C. Ho
(74) Attorney, Agent, or Firm—McDermott Will & Emery

(57) ABSTRACT

The present invention provides a method and system for determining the position of the image of a target object or the position of the x-ray source in digital tomosynthesis, as the x-ray source is moved relative to the object so as to obtain multiple two-dimensional images of the object from multiple angles. At least one marker, characterized by a simple and known image pattern, is disposed between an x-ray source and a detector system. The shift in the image of the object, resulting from the movement of the x-ray source during tomosynthesis, is calculated to a desired resolution using the readily observable shift in the image of the marker. The x-ray source may be translated along a plane parallel to the plane of the detector system, or may be rotated about a fixed center.

19 Claims, 7 Drawing Sheets

IMAGE POSITIONING METHOD AND SYSTEM FOR TOMOSYNTHESIS IN A DIGITAL X-RAY RADIOGRAPHY SYSTEM

CROSS REFERENCES TO RELATED APPLICATIONS

This application claims the benefit of priority under 35 U.S.C. §119(e) from co-pending, commonly owned U.S. provisional patent application Ser. No. 60/316,511, entitled "A Digital X-Ray Radiography System For Tomosynthesis," filed on Aug. 31, 2001.

STATEMENT OF GOVERNMENT INTEREST

The U.S. Government has no interest in or to this patent.

FIELD OF THE INVENTION

The present invention relates generally to tomosynthesis, and more particularly to an image positioning method and system for digital tomosynthesis.

BACKGROUND

Standard x-ray radiography allows an x-ray image of a target object to be obtained, by capturing x-rays transmitted through the object onto a film screen. The x-ray image is a projection of the object along the x-ray direction. In the x-ray image, variations in the composition and thickness of the target object in different regions of the object are revealed, as a result of their differential absorption of the x-rays.

Digital radiography allows x-ray images to be captured digitally. Typically, an array of digital detectors and a digital image processor are used. Digital radiography systems allow the radiologist to window the image, i.e. to adjust the image's contrast. In this way, subtle details, which may be missed by the fixed, limited contrast in traditional film-screen radiography, can be detected. Thus, digital x-ray systems produce images having a greatly enhanced contrast, compared to the contrast in the images obtained by traditional film-screen radiography. the resolution of digital x-ray images is also greatly enhanced compared to the resolution of images obtained using other techniques, for example CT scanning.

There is no depth information, however, in the images obtained by stationary two-dimensional arrays of digital detectors, unlike in the images obtained by CT scanning. Digital x-ray systems produce 2-D images of the object, as projected along the x-ray direction and onto a lateral plane parallel to the plane formed by the detectors. These 2-D images have no resolution in the longitudinal dimension parallel to the x-ray beam and orthogonal to the detector plane formed by the detectors.

Digital tomosynthesis enables a three-dimensional (3-D) image of an object to be constructed from a finite set of 2-D projection images of the object, by acquiring multiple 2-D images from multiple angles, and then reconstituting the data. Using digital tomosynthesis, a certain degree of resolution can be produced in the longitudinal dimension. Typically, in digital tomosynthesis systems the x-ray source is rotated during data acquisition, for example in an arc through a limited angular range, and a set of projection radiographs of the object are acquired by a stationary detector at discrete locations of the x-ray source. In many systems, the digital x-ray detector array and the object are maintained in a stationary or fixed position, while the x-ray source is moved to multiple locations in order to obtain a collection of images from different view angles.

The multiple 2-D images are then combined or synthesized, using known digital averaging and filtering techniques. Each synthesized image is focused on a tomography plane, which is parallel to the detector plane, and which is located at a certain depth along the longitudinal direction. In a simplest method, the 2-D projection images are spatially translated with respect to each other, and superimposed in such a way that the images overlap precisely in the tomography plane. Other methods for reconstructing tomographic images may use sophisticated computation techniques similar to those used in computerized tomography (CT) systems. The location of the tomography plane within the object can be varied, and a 2-D image of the object can be obtained for each location of the tomography plane.

One of the drawbacks of digital tomosynthesis is that the relative location of the x-ray source with respect to the detector array must be known with great precision, as the x-ray source is being moved with respect to the object being imaged. In the process of synthesizing the images, it is necessary to align the collected images with a precision equal to, or better than, the lateral resolution. It is difficult, however, to move the x-ray source to multiple positions with the requisite degree of precision. Uncertainties in the position of the x-ray source and/or the x-ray detector generally contribute to image blurring.

Accordingly, it is desirable to provide a high-precision image positioning method and system for digital tomosynthesis that allows the position of the x-ray source and the object to be determined within a desired resolution, without requiring precise physical positioning of the x-ray source at the desired resolution. Such high-precision image positioning method and system would greatly reduce the mechanical requirement of the imaging system for tomosynthesis.

SUMMARY OF THE INVENTION

The present invention features a high-precision image positioning method and system for tomosynthesis, in a digital x-ray radiography system. In the present invention, the image of one or more high-precision markers is used to calculate the required shift in a collection of 2-D images of an object, as the x-ray source is moved in order to generate a plurality of 2-D images from multiple viewing angles. The method and system of the present invention thus allows the necessary shift to be calculated at high precision for each of the plurality of images used in digital tomosynthesis, without requiring the x-ray source to be accurately positioned, each time it is moved.

A high-precision image positioning system in accordance with the present invention includes an x-ray source for generating x-rays directed toward a target object, a digital x-ray detector system disposed in a detector plane, and one or more markers disposed between the x-ray source and the detector system. The markers are configured in accordance with a specific design. The digital detector system detects x-rays transmitted through the object, and generates object image data for an image of the object projected along the detector plane.

Preferably, the marker is configured in a simple and known pattern, on a plane parallel to the detector plane. The position of the marker is fixed with respect to the detector. The detector detects the x-rays transmitted through the marker, and generates marker image on the detector plane.

Because of the simple and known image pattern, the marker image data are easily identifiable by a computer program.

A translation of the x-ray source within a lateral plane parallel to the detector plane produces a corresponding shift in the image of the marker. The shift in the image of the object, which results from the displacement of the x-ray source, can be calculated from the readily observable shift in the image of the marker, and from the known distance of the object from the detector plane along a longitudinal direction parallel to the x-rays.

The x-ray source may be moved in both the x- and y-directions within the lateral plane, in order to improve the image quality of the resulting synthesized image. In this case, multiple markers are used, in order to detect the shifts in both the x- and y-directions. Markers may also be used in a tomography system having a rotating x-ray source, in order to detect the rotation angle of the x-ray source.

BRIEF DESCRIPTION OF THE DRAWINGS

The invention can be more fully understood by referring to the following detailed description taken in conjunction with the accompanying drawings. The drawing figures depict preferred embodiments by way of example, not by way of limitations. In the figures, like reference numerals refer to the same or similar elements.

DETAILED DESCRIPTION OF THE PREFERRED EMBODIMENTS

The present invention features a method and system for aligning the two-dimensional image data in a digital tomosynthesis system. In the present invention, the shift required for each 2-D image used in digital tomosynthesis to synthesize or reconstruct a 3-D image is calculated, using the image of one or more markers having a specifically designed pattern.

Figure 1:
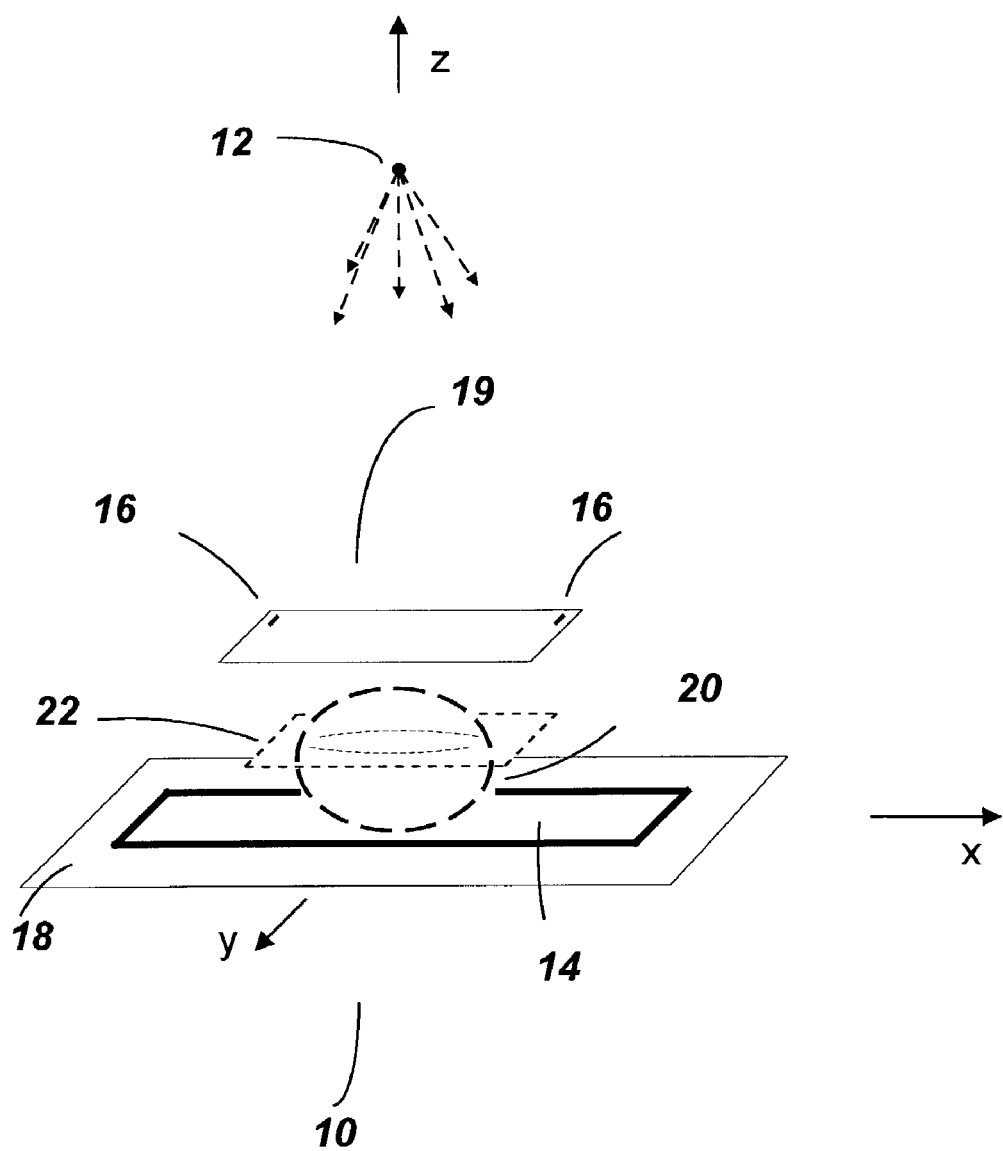
FIG. 1 schematically illustrates a tomosynthesis system, constructed in accordance with one embodiment of the present invention, and including a marker for tracing the displacement of the x-ray source.

FIG. 1 schematically illustrates a digital tomosynthesis system 10, constructed in accordance with one embodiment of the present invention. In overview, the system 10 includes a radiation source 12, a radiation detector system 14, and at least one marker 16 disposed between the radiation source 12 and the radiation detector system 14. Preferably, the radiation source is an x-ray source 12, and the radiation detector system is a planar digital x-ray detector system 14 lying in a detector plane 18. The x-ray source 12 generates x-rays that are transmitted through a target object 20 that is being imaged. The target object 20 is disposed in the path of x-rays propagating from the source 12 to the detector system 14. The target object 20 may be a portion of the human body, for example a breast in mammography systems.

The x-ray detector system 14 receives x-rays that have passed through the object 20, and generates intensity signals related to the intensity of the transmitted x-rays. The detector system 14 is preferably a planar detector array, and includes a two-dimensional planar array of x-ray detection elements lying in the detector plane 18. In one form, each of the detection elements may include a scintillator element, responsive to incident x-rays to produce light photons, and a photodiode which produces a digitized signal representation of the x-ray flux incident on the scintillator element. Alternatively, the system 14 may be a direct digital detector system, in which x-ray signals are converted into digital images at the detection elements themselves, the images being digitized into a matrix of pixels, and each pixel being coded digitally.

The system 10 may also include a digital image processor [not shown] connected to the detector system 14 for processing data produced by the detector system 14 in response to incident x-rays, so that an image of the object projected on the detector plane 18 can be constructed. The system 10 may further include a motion controller [not shown] for moving the x-ray source 12 during tomosynthesis.

Tomosynthesis allows reconstruction of the image of any plane within the target object that is parallel to the detector plane 18. A finite set of 2-D projection images, which are acquired from multiple viewing angles corresponding to different positions of the x-ray source 12, are spatially translated with respect to each other. In the simplest reconstruction method, these 2D projection images are superimposed in such a way that the images of the object overlap exactly in a desired tomography plane 22. Other reconstruction methods require more sophisticated computations, thus also require high precision in the alignment of these 2D projection images. The tomography plane 22 is parallel to the detector plane 18. Preferably, the detector plane 18 is defined by mutually perpendicular x- and y-coordinate axes, as indicated in FIG. 1.

The tomography plane 22 is located at a certain depth along a longitudinal direction (shown as the z-coordinate in FIG. 1) orthogonal to the detector plane 18. In the simplest reconstruction method, the location of the tomosynthesis plane 22 within the object can be varied along the z-axis by varying the amount of relative translation of the projection images. Each time the tomosynthesis plane 22 is varied, the image data corresponding to the overlapping structures are superimposed exactly at the new location of the tornosynthesis plane, so that a two-dimensional image of the object, as focused in the desired tomosynthesis plane, can be obtained. A 3-D image of the object is generated from the resulting set of synthesized 2-D images, focused at each desired location of the tomography plane 22.

In the process of synthesizing images in each tomography plane 22, it is necessary to align the collected images with a precision equal to, or better than, the lateral resolution of the detector system 14. Each time the x-ray source 12 is moved during tomosynthesis, therefore, the relative location of the x-ray source 12 with respect to the detector array must be known with great precision, in order to correctly align each of the collected images in the tomography plane 22. Typically, the spacing between adjacent detector elements in the detector array may be about 50 microns, and the corresponding lateral image resolution may be in the order of around 0.1 mm. It is very difficult to move the x-ray source 12 to multiple positions with a precision corresponding to such orders of magnitude.

The present invention relies on one or more precisely designed markers 16, placed between the x-ray source 12 and the detector array 14, to trace the position of the x-ray source 12 as the source is moved to multiple locations. In this way, accurate positioning of the x-ray source 12 is not necessary, and the mechanical requirements of the tomosynthesis system 10 is greatly reduced. In a preferred embodiment, the marker 16 is disposed on a lateral plane 19 parallel to the detector plane 18, as illustrated in FIG. 1, which shows the relative geometry of the x-ray source 12, the marker 16, the object being imaged, and the detector array 14. Preferably, the locations of the one or more markers 16 are fixed with respect to the detector array 14 during collection of multiple images. Preferably, the image of the marker 16 does not overlap with the image of the target object 20. Therefore, the marker 16 is preferably placed near the edge of the field of view.

Figure 2:
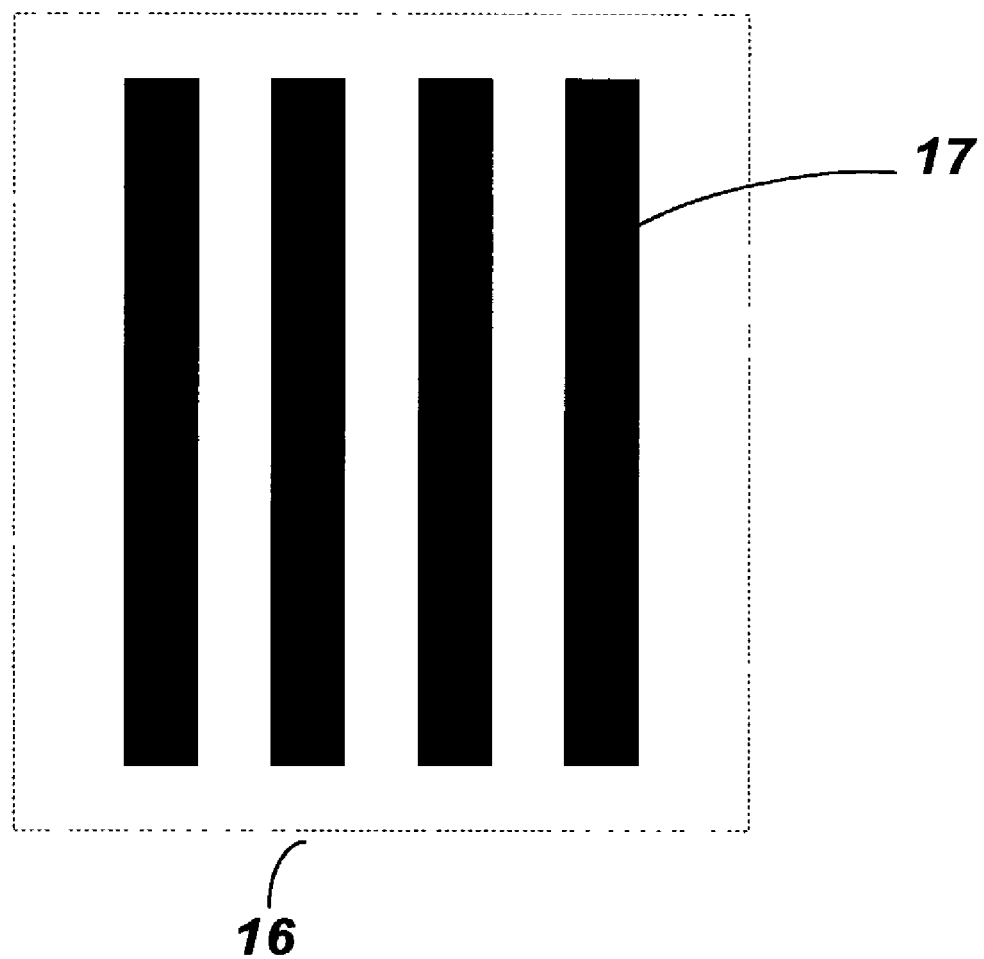
FIG. 2 illustrates a marker constructed in accordance with one embodiment of the present invention, and including four stripes of high-contrast material.

The marker 16 is characterized by a simple and known pattern, and can thus be easily identified from the image data. The location of the marker 16 can thus be accurately calculated from the image data. FIG. 2 illustrates a marker 16 constructed in accordance with one embodiment of the present invention. The marker 16 is preferably constructed from a high-contrast material, and includes a set of stripes or wires in a pre-defined pattern. In the embodiment illustrated in FIG. 2, the marker 16 consists of four straight and parallel stripes 17 of high-contrast material, which may include, but is not limited to, metal. The marker 16 may be fabricated using printed circuit technology, for example. The marker 16 leaves a signature like a simple barcode in the image data, from which the position of the x-ray source 12 can be traced. In other words, the easily identifiable image of the marker 16 is used as a measure of the relative position of the x-ray source 12.

Figure 3:
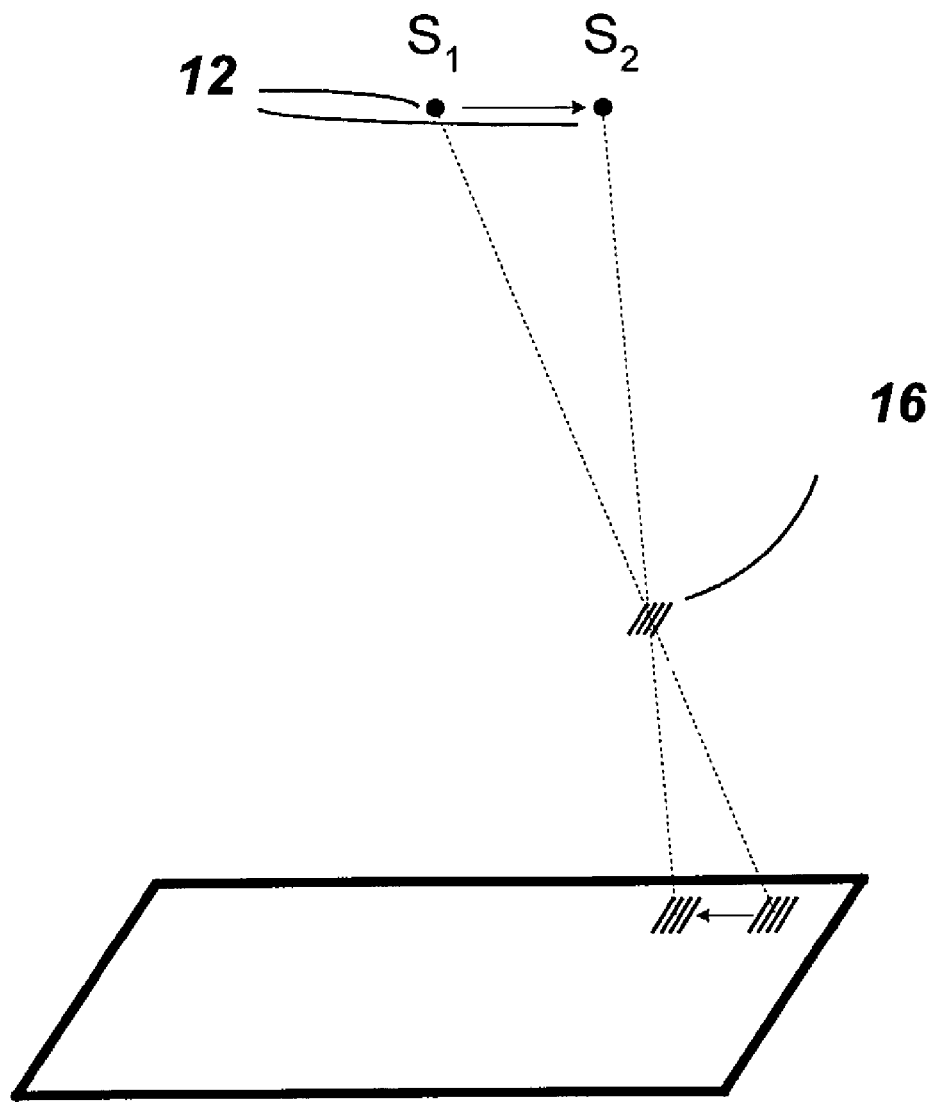
FIG. 3 illustrates the correlation between a lateral displacement of the x-ray source and the resulting shift in the image of the marker.

As the x-ray source is moved laterally (i.e. within a lateral plane parallel to the detector plane) from one position to another, the image of the marker shifts from one location of the detector array to another. FIG. 3 illustrates the correlation between a lateral displacement of the x-ray source 12 and the resulting shift in the image of the marker 16. For simplicity, a lateral displacement along the x-direction from a position S1(x1) to S2(x2) is shown. As shown in FIG. 3, when the x-ray source 12 is moved in a lateral direction perpendicular to the stripes on the marker, the image of the marker 16 is shifted sideways.

Figure 4:
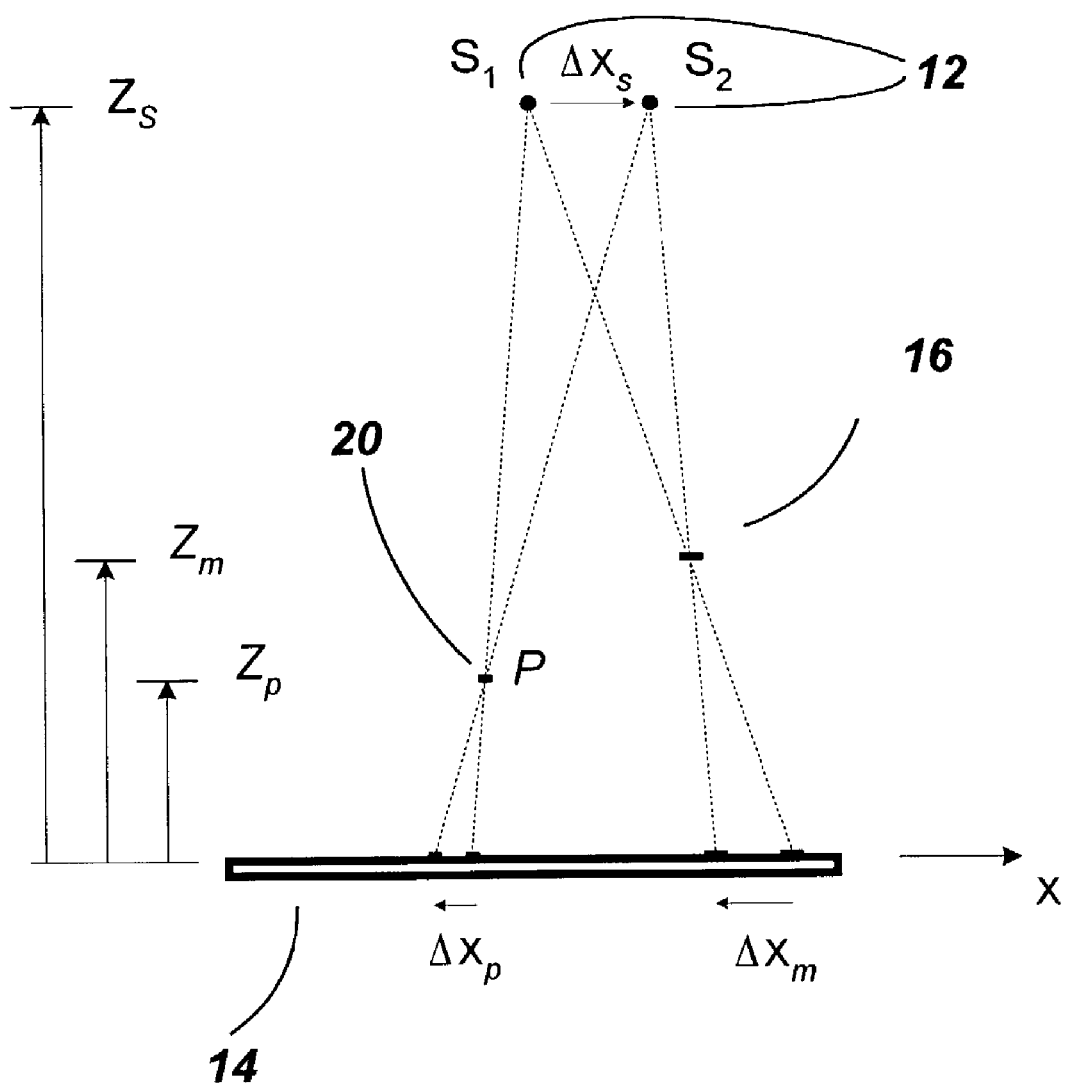
FIG. 4 illustrates the lateral shifts in the images of a marker and a point within the target object, which result from a lateral displacement of the x-ray source.

FIG. 4 illustrates the lateral shifts in the images of a marker 16 and a point of interest P within the object 20, resulting from a lateral displacement of the x-ray source 12. If the x-ray source 12 is translated on a plane parallel to the detector array 14, the relationship between the shift of the marker's image and the displacement of the x-ray source 12 is simple, and independent of the lateral location of the source 12. In the embodiment illustrated in FIG. 4, the x-ray source 12 is moved from position at S1(x1) to S2(x2) along a lateral direction, namely the direction of the x-axis. As can be seen from the geometrical configuration illustrated in FIG. 4, the displacement of the x-ray source 12 is related to the shift in the marker's image by $$\Delta Xs = \Delta Xm^*(Zs-Zm)/Zm. \tag{1}$$

In equation (1) above, $\Delta Xs$ represents the displacement of the x-ray source 12; $\Delta Xm$ represents the shift in the image of the marker 16 resulting from the displacement of the x-ray source 12. Also, $Zs$ and $Zm$ represent the longitudinal distances of the x-ray source 12 and the marker 16, respectively, from the detector plane, i.e. the distances of the x-ray source and the marker from the detector plane along a longitudinal direction perpendicular to the detector plane (illustrated in FIG. 4 as the z-direction). In FIG. 4, $Zs$ and $Zm$ are illustrated as the z-coordinates of the x-ray source 12 and the marker 16, respectively, As seen from FIG. 4, if P is a point of interest in the object being imaged, the image location of this point P is shifted by $$\Delta Xp = \Delta Xs^* Zp/(Zs-Zp). \tag{2}$$

In equation (2) above, $\Delta Xp$ represents the shift in the image of the point P within the object 20, resulting from the displacement of the x-ray source 12; and $Zp$ represents the longitudinal distance of the point P, i.e. the distance of the point P from the detector plane along the z-direction. ($\Delta Xs$ and $Zs$ represent the same as discussed in conjunction with equation (1) above). Using equation (1) in equation (2), the shift in the image of P is related to the shift in the image of the marker by $$\Delta Xp = \Delta Xm^*(Zp/Zm)^*(Zs-Zm)/(Zs-Zp) \tag{3}$$

In equation (3), the distance $Zm$ is greater than $Zp$. The last factor in Equation (3) is therefore always less than 1.

Equation (3) shows that the shift in the image of any point of interest within the object 20 is correlated by a simple and known relationship to the lateral shift in the image of the marker 16. This shift is readily identifiable and calculable, as discussed above in paragraph 32. As seen in Equation (3), the shift in the image of point P within the object can be easily determined from the lateral shift $\Delta Xm$ of the marker 16, and the longitudinal distances of the point P, the x-ray source 12, and the marker 16, respectively, from the detector plane. The shift in the image of point P can thus be determined, without repeatedly having to determine the position of the x-ray source with extreme precision.

As long as the x-ray source 12 moves within the same lateral plane parallel to the detector array 14, the shifts $\Delta Xm$ and $\Delta Xp$ are independent of the x- and the y-coordinate location of the x-ray source 12 within the lateral plane. In this kind of a tomosynthesis system, every pixel of the same image is shifted by the same amount while being synthesizing with other images, thereby simplifying tomosynthesis calculations considerably.

In the present invention, the shift in the image of an object point P can be calculated with a resolution comparable to the lateral resolution of the detector system 14, by using the marker 16. If the shift in the image of the marker, $\Delta Xm$, is calculated with an error of $\Delta Xm$, the resultant error in the shift of object, $\Delta Xp$, can be expressed as $$\delta p \leq \delta m^*(Zp/Zm) \tag{4}$$

Thus, for example, if the z-coordinate of the point is half way between the marker 16 and the detector array 14, the uncertainty in the object's shift is less than half of the error in the marker's shift.

From Equation (4), it appears that as the marker 16 is placed closer to the x-ray source 12, the error in determining the shift in the image of the object 20 is reduced. In practice, this is not necessary true. Because the x-ray source 12 has a finite size in a focal spot within an anode inside the source, the sharpness of the image diminishes, as the marker 16 is moved closer to the x-ray source 12. Consequently, the accuracy in the location of the marker's image is decreased. Also, the shift in the image of the marker 16 increases, so that the marker's image becomes more likely to overlap with the object's image.

In the lateral dimension, the marker 16 can be placed anywhere within the field of view and preferably out of the object's region. In the longitudinal dimension, the marker's z-position affects the accuracy of the calculated shift in the object's image. If the error of the marker's z-position is δ(Zm), the error in the object's lateral shift is given by:

$$\delta(\Delta Xp) \cong Xp * \delta(Zm)/Zm \qquad (5)$$

In equation (5) above, an approximate value of 1 is used for the last factor of Equation (3).

As seen from equation (5) above, the error in the marker's z-position introduces the same degree of error in the lateral shift in the image of the object 20. The lateral shift is used to align the image for generating a tomosynthesis image targeted at a tomography plane located at a certain depth (i.e. z-coordinate value) of the object. An error in the lateral shift is equivalent to an error in the targeted depth. If the shift ΔXp is used for the tomosynthesis, the error is reflected in the depth by $$\delta(Zp) \cong \delta(Zm) * (\Delta Xp / \Delta Xm). \qquad (6)$$

As seen from equation (6) above, the error δ(Zp) in the longitudinal distance (along the z-direction) of the point P within the object is independent of the lateral location of the object. As long as the shift of the marker 16 is calculated accurately from the image data, therefore, all pixels of the image will align accurately with other images in generating a synthesized image. Because of the uncertainty δ(Zm) in the z-position of the marker 16, however, the depth of the synthesized image is offset by δ(Zp), for all pixels. A small uncertainty in the depth (or z-coordinate) of the synthesized image is not a concern, however. If equal spacing is used in selecting the z-coordinate Zp of the point P, for computing the shift ΔXp in the image of the point P, the synthesized images will still have equal spacing in depth. The accuracy of the marker's z-position along the z-direction therefore does not affect the image quality of the tomosynthesis images. The marker 16 should, however, be maintained in a fixed position relative to the detector array, during the course of taking multiple exposures from the x-ray source at different locations.

The accuracy of the measurement of the shift in the image of the point P in the object depends on the specific image pattern of the marker 16, and the calculation algorithm. A marker with stripes along the direction of the detector column casts its image on multiple rows of the detector array. Depending on the alignment of the stripe with the column, the shift can be calculated for each row and then averaged from multiple rows, or the image data can be averaged first before calculating the shift. The simplest example of a marker is a single stripe. In that case, the centroid of the marker's image intensity can be calculated from one or more rows of image data to be the location of the marker.

Figure 5:
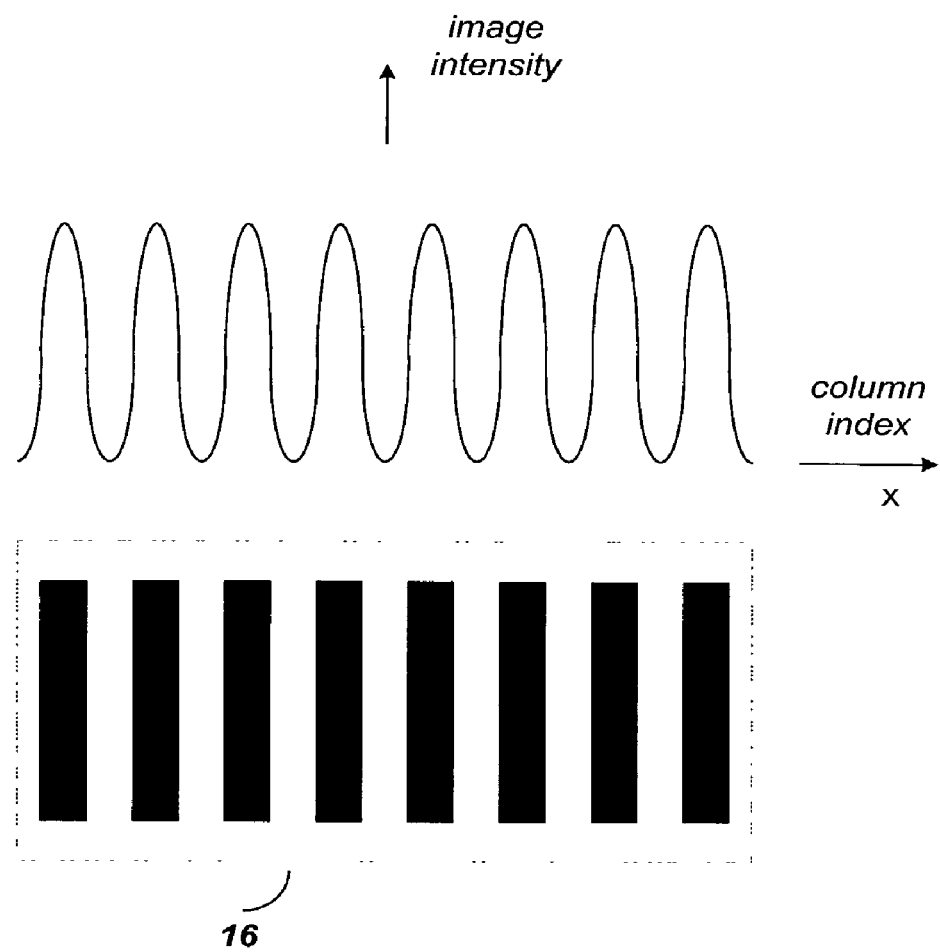
FIG. 5 illustrates a marker having a plurality of equally spaced stripes, and a resulting image intensity characterized by a periodic pattern.

A more complicated pattern consists of multiple stripes, with equal spacing between the stripes. FIG. 5 illustrates a marker 16 having a plurality of equally spaced stripes, and a resulting image intensity characterized by a periodic pattern. In this case, the image intensity is a periodical function along the direction of a detector row. The phase information in the image intensity function can be used to determine the image location, within a precision that is of the order of a fraction of the detector spacing. As mentioned earlier, the detector spacing may typically be in the order of about 50 microns. In other words, the marker produces a phase-encoded signal on the image. The phase information calculated from the image data provides the details necessary for locating the marker image from the image data, with fine precision.

Depending of the size and positioning of the object, the image of the marker 16 may occasionally overlap with the outer regions of the image of the object 20. Because the image pattern of the marker 16 is known a priori, it is possible to remove the image of the marker 16 from the image of the object 20. The removal process is even simpler if the image of the marker is not overlapped with the image of the object.

In a preferred embodiment of the invention, the x-ray source 12 is translated along another lateral direction, i.e. the y-direction, in addition to being translated along the x-direction. In this way, additional image data can be acquired for the tomosynthesis process. The same type of marker 16 is preferably used to measure and calculate the shift required in the other lateral direction (y-direction) for tomosynthesis. When the x-ray source 12 is translated along the y-direction, the orientation of the marker 16 is rotated so that the pattern formed by the parallel stripes line up along the y-direction. In this embodiment, one or more markers 16 are used for measuring the shift of the image of the object 20 in the x-direction, and one or more separate markers are used for measuring the shift of the object image in the y-direction.

Figure 6:
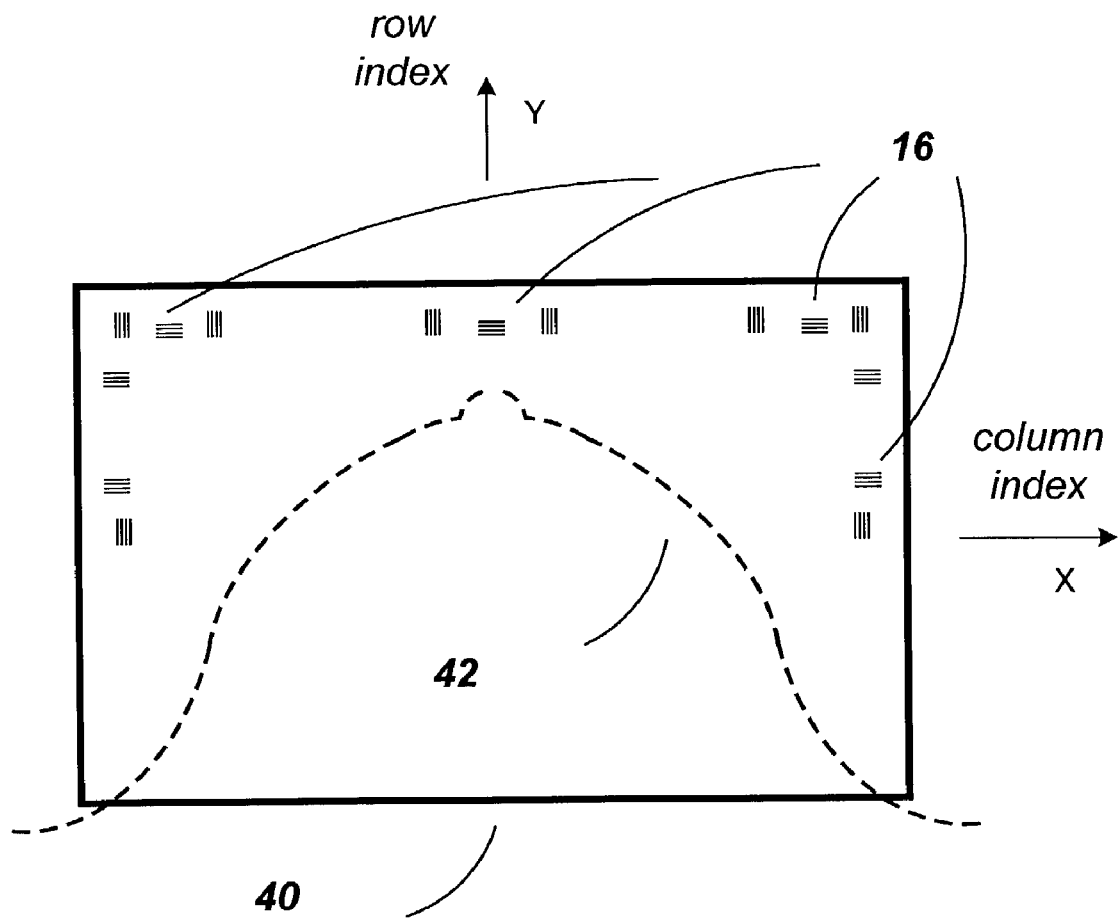
FIG. 6 illustrates a mammography system including a plurality of markers for measuring shifts in the images of the object and the x-ray source in both the x- and the y-directions.

FIG. 6 illustrates a mammography system including a plurality of markers 16 for measuring shifts in the images of the object and the x-ray source 12 in both the x- and the y-directions. In a mammography system, a compression plate 40 is typically used, in order to compress the patient's breast 42 to flatten the breast 42 and make it easier to be imaged. When the method and system of the present invention is used in such a mammography system, the marker 16 is preferably mounted on the surface of or inside the compression plate 40. As mentioned earlier, the markers 16 are preferably placed near the edges of the field of view to avoid overlapping with the object being imaged.

In the embodiment illustrated in FIG. 6, a plurality of markers 16 are used, in order to measure shifts in both the x- and the y-directions. When moving the x-ray source 12 during tomosynthesis, the x-ray source 12 may not translate perfectly along the x-direction. A deviation to the y-direction will cause a misalignment of the images in the y-direction. It is therefore preferable to measure and use shifts in both the x- and the y-directions for tomosynthesis, whether the x-ray source 12 is translated in one lateral dimension or two.

It is also preferable to use markers at multiple locations, in order to measure the shift in each direction. In this way, redundant data can be obtained so that the image locations can be calculated more accurately. Furthermore, a marker 16 may get out of the field of view at certain angles of the x-ray. In this case, the other marker at the other end provides a cover. Likewise, a marker may fall into the object region at certain angles and become less accurate in measuring the shift. In this case, the other marker 16 enhances the accuracy of the measurement.

Figure 7:
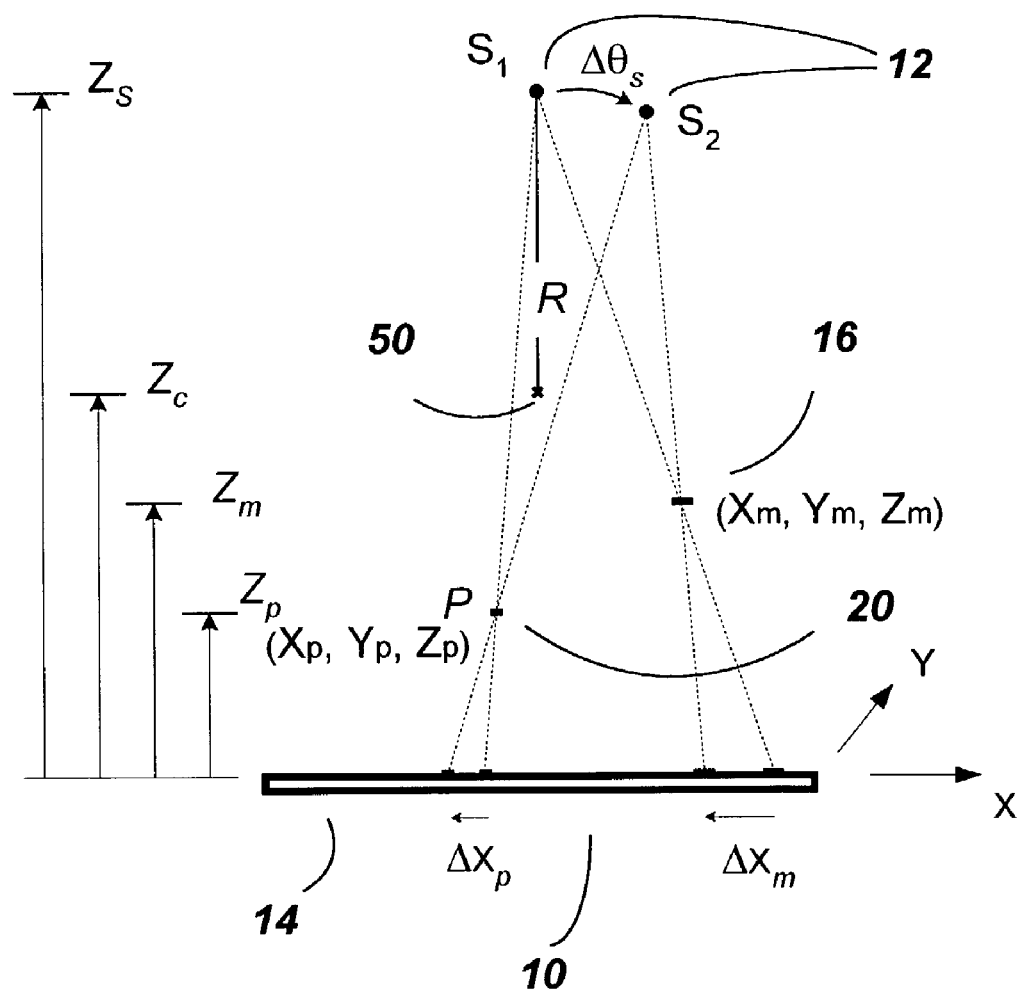
FIG. 7 illustrates the shifts in the images of a marker and an object in a digital tomosynthesis system constructed in accordance with one embodiment of the present invention, and including an x-ray source that is rotated with respect to a fixed center.

In another preferred embodiment of the invention, the x-ray source 12 is rotated, rather than being translated. FIG. 7 illustrates the shifts in the images of a marker 16 and an object 20 in a digital tomosynthesis system 10 that includes a rotating x-ray source 12. In the system 10, the x-ray source 12 is rotated about a fixed rotation center 50, which is located at a distance R from the x-ray source 12. The requisite shift in the image of an object 20 for performing tomosynthesis depends on the rotation angle θs and radius R. Assuming the radius R is known precisely and held constant all the time, the shift needed for a point P in the object 20 at a location (Xp, Yp, Zp) depends on the change in rotation angle, Δθs, and on the lateral coordinate Xp. But, unlike in the case of planar translation (represented by equation (3) in paragraph 35), the shift also depends slightly on the lateral coordinate Yp and the longitudinal coordinate Zp. Qualitatively, it can be expressed as a function g of these variables as $$\Delta Xp = g(\Delta\theta s, Xp, Yp, Zp) \qquad (7)$$

The change in the rotation angle can be derived from the shift in the marker's image by a function $f$, namely, $$\Delta\theta s = f(\Delta Xm) \qquad (8)$$

Accordingly, the shift in the image of the point P within the object can be obtained from the shift of the marker's image according to a function h as follows:

$$\Delta Xp = h(\Delta Xm, Xp, Yp, Zp) \qquad (9)$$

In equations (8) and (9) above, the lateral coordinates (i.e., Xp, Yp, Xm, and Ym) are measured against the center of the rotation. Also, in Equation (8) Δθs depends on Xm, Ym, and Zm. Although the x-, y-, and z-coordinates are held constant throughout the multiple exposures at different rotation angles, the error in setting these constants in Equation (9) will introduce a corresponding error in ΔXp. Unlike the case in which the x-ray source 12 is translated within a lateral plane, such an error depends on Xp and Yp. As the result, the effect of focusing at a targeted depth varies across the lateral dimension. In other words, the focusing is not as sharp and uniform as in the case of a planar translation of the x-ray source 12. In addition, the focused region is deviated from a plane.

In the embodiment illustrated in FIG. 7, the marker's image is used to measure the rotation angle with high precision. The rotation angles for multiple exposures do not have to be precise. However, the location of the detector and the location of the marker with respect to the center of rotation must be known fairly accurately, and must be held constant.

In sum, the present invention features a method and system for aligning image data for tomosynthesis in a digital radiography system. The method and system of the present invention does not require precise and reproducible positioning of the x-ray source during tomosynthesis. The image of one or more precisely designed markers are used as traces to calculate the amount of lateral shift required for each of the collection of images used to generate a synthesized image. While the marker's location need not be known with precision, it is important that the marker be maintained at a same location with respect to the detector array, during multiple exposures of the x-rays from different locations of the x-ray source.

While the invention has been particularly shown and described with reference to specific preferred embodiments, it should be understood by those skilled in the art that various changes in form and detail may be made therein without departing from the spirit and scope of the invention. It is understood that various modifications may be made therein and that the invention or inventions may be implemented in various forms and embodiments, and that they may be applied in numerous applications, only some of which have been described herein. As used herein, the terms "includes" and "including" mean without limitation. It is intended by the following claims to claim any and all modifications and variations that fall within the true scope of the inventive concepts.

What is claimed is:

1. A method for aligning an image of a target object for tomosynthesis in a x-ray radiography system of the type including an x-ray source, and an x-ray detector system for detecting x-rays emitted from the x-ray source and transmitted through said object, comprising:
   a. positioning at least one marker between said x-ray source and said detector system;
   b. moving said x-ray source after step a; and
   c. measuring a shift in the image of the at least one marker caused by said motion of said x-ray source;
   d. correlating the shift measured in step c with a corresponding shift in the image of a point of interest in the target object, thereby determining a shift in the image of the point of interest in the target object caused by said motion of said x-ray source.

2. A method according to claim 1, wherein said detector system is disposed in a detector plane, and wherein the step of moving said x-ray source comprises at least one of:
   i) translating said x-ray source within a lateral plane parallel to said detector plane; and
   ii) rotating said x-ray source about a fixed center.

3. A method according to claim 1, wherein the step of positioning said at least one marker comprises positioning a plurality of markers at a plurality of locations between said x-ray source and said x-ray detector so as to generate data for redundant measurements of said shift in said image of the target object.

4. A method according to claim 1, wherein in step b, the x-ray source is translated within a lateral plane parallel to the detector plane, and wherein the step of determining a shift in the image of the target object comprises the step of calculating the relationship between said shift in the image of the object and said shift in the image of said marker.

5. A method according to claim 4, wherein said relationship is given by:

$$\Delta X_{p} = \Delta X_m * (Z_p/Z_m) * (Z_s - Z_m)/(Z_s - Z_p),$$

where
   $\Delta X_p$ is the shift in the image of a point of interest within the object;
   $\Delta X_m$ is the shift in the image of the marker;
   $Z_s$ is the distance of the radiation source from a detector plane defined by said detector system, as measured along a longitudinal direction orthogonal to said detector plane;
   $Z_m$ is the distance of the marker from said detector plane as measured along said longitudinal direction; and
   $Z_p$ is the distance of the point of interest from said detector plane along said longitudinal direction.

6. A method according to claim 1, wherein the marker comprises a plurality of linear parallel stripes disposed along a direction parallel to a detector plane defined by said detector system.

7. A method according to claim 1, wherein said x-ray radiography system comprises a digital x-ray radiography system, and wherein said x-ray detector system comprises a digital x-ray detector system.

8. An apparatus for obtaining tomosynthesis data of an object, the apparatus comprising:
   a. an x-ray source for generating radiation directed toward said object;

b. an x-ray detector system disposed in a detector plane for detecting radiation transmitted through said object and for generating object image data representative of an image of said object on said detector plane; and c. at least one marker disposed between said x-ray source and said detector so that the detector system can receive x-rays transmitted through the marker to generate marker image data representative of an image of the marker on the detector plane;

wherein the x-ray source is disposed at a distance $Z_s$ from said detector plane, as measured along a longitudinal direction orthogonal to said detector plane;

wherein the marker is disposed at a distance $Z_m$ from said detector plane as measured along said longitudinal direction;

wherein $Z_s$ and $Z_m$ are selected so as to avoid overlap between the image of the object and the image of the marker, and so that when the x-ray source is moved after the marker is disposed between the x-ray source and the detector system, a shift $\Delta X_p$ in the image of a point of interest P in the object on said detector plane, resulting from the motion of said x-ray source, is correlated to a corresponding shift $\Delta X_m$ in the image of said marker on said detector plane by a relationship given by:

$$\Delta X_p \Delta X_m * (Z_p/Z_m) * (Z_s-Z_m)/(Z_s-Z_p),$$

where $Z_p$ is the distance of the point of interest P from said detector plane along said longitudinal direction, and wherein the marker comprises a plurality of linear parallel stripes disposed along a direction parallel to said detector plane.

9. An apparatus according to claim 8, wherein said stripes are made of relatively high contrast material.

10. An apparatus according to claim 8, wherein said detector comprises an array of rows and columns of detector elements;

and wherein said marker comprises a plurality of linear and parallel stripes disposed along a direction parallel to at least one of said rows of detector elements.

11. An apparatus according to claim 10, wherein the image intensity of said marker forms a periodic signal along the direction of said row of detector elements.

12. An apparatus according to claim 11, wherein said period signal contains phase shift information indicative of the position of the image of the marker.

13. An apparatus according to claim 8, further comprising a digital image processor for processing said object image data to construct an image of said object on said detector plane.

14. An apparatus according to claim 8, further comprising a motion controller for moving said x-ray source relative to said object to a plurality of positions within a lateral plane parallel to said detector plane.

15. An apparatus according to claim 8, wherein said x-ray source is a movable x-ray source, and said x-ray detector is a stationary detector.

16. An apparatus according to claim 8, wherein said x-ray source and said x-ray detector system are part of a mammography system having a compression plate, and wherein said marker is disposed inside said compression plate.

17. An apparatus according to claim 8, wherein said x-ray source and said x-ray detector system are part of a mammography system having a compression plate, and wherein said marker is disposed on an outer surface of said compression plate.

18. An apparatus according to claim 8, wherein said at least one marker is disposed in proximity to an outer boundary of the field of view of said radiation detector, so that spatial overlap between the image of said marker and the image of said object is prevented.

19. An apparatus for obtaining tomosynthesis data of an object, the apparatus comprising:

A. an x-ray source for generating radiation directed toward said object;

B. an x-ray detector disposed in a detector plane, the detector being adapted to detect x-rays transmitted through said object and to generate object image data for an image of said object on said detector plane; and C. at least one marker disposed between said x-ray source and said detector at a fixed location with respect to said detector so that the detector is responsive to x-rays transmitted through said marker to generate marker image data representative of an image of the marker on said detector plane;

wherein a displacement of said x-ray source within a lateral plane parallel to said detector plane produces a corresponding lateral shift in said image of the marker; and wherein a shift in the image of a point of interest within the object, resulting from said displacement of said x-ray source, is correlated by a known relationship to said shift in said image of the marker, and to the distance of said point of interest from said detector plane along a longitudinal direction orthogonal to said detector plane; and wherein said lateral plane is defined by mutually perpendicular x- and y-coordinate axes;

wherein said at least one marker comprises:

a) at least a first marker that includes a plurality of linear and parallel stripes disposed along an x-direction parallel to said x-coordinate axis; and b) at least a second marker that includes a plurality of linear and parallel stripes disposed along a y-direction parallel to said y-coordinate axis;

wherein a displacement of said radiation source along the x- and y-directions, respectively, produces corresponding shifts in the image of said first and said second markers along the x- and the y-directions, respectively;

wherein the shift along the x-direction in the image of a point of interest within the object, resulting from a displacement of said radiation source along the x-direction, is correlated by a known relationship to the shift in the image of said first marker along the x-direction; and wherein the shift along the y-direction in the image of a point of interest within the object, resulting from a displacement of said radiation source along the y-direction, is correlated by a known relationship to the shift in the image of said second marker along the y-direction.

* * * * *

UNITED STATES PATENT AND TRADEMARK OFFICE
CERTIFICATE OF CORRECTION

| | |
|---|---|
| PATENT NO. | : 6,960,020 B2 |
| APPLICATION NO. | : 10/232266 |
| DATED | : November 1, 2005 |
| INVENTOR(S) | : Ching-Ming Lai |

It is certified that error appears in the above-identified patent and that said Letters Patent is hereby corrected as shown below:

Column 10, line 42: should read  $\Delta X_p = \Delta X_m * (Z_p / Z_m) * (Z_s - Z_m)/(Z_s - Z_p)$ Column 11, line 26: should read  $\Delta X_p = \Delta X_m * (Z_p / Z_m) * (Z_s - Z_m)/(Z_s - Z_p)$ Signed and Sealed this Twenty-second Day of August, 2006

JON W. DUDAS
*Director of the United States Patent and Trademark Office*